United States Patent [19]
Ishibe et al.

[11] Patent Number: 5,230,348
[45] Date of Patent: Jul. 27, 1993

[54] GUIDE WIRE FOR A CATHETER

[75] Inventors: Hideomi Ishibe, Kyoto; Jun Matsuda; Tamotsu Karaki, both of Hirakata; Yukoh Yamada, Funabashi; Teruo Hashimoto, Kuki; Kazunori Kamishohara, Nerima, all of Japan

[73] Assignees: Nippon Seisen Co., Ltd., Osaka; DIA Medical Supply, Inc., Saitama; Clinical Supply Co., Ltd., Gifu, all of Japan

[21] Appl. No.: 775,814

[22] Filed: Oct. 11, 1991

[30] Foreign Application Priority Data

Oct. 12, 1990 [JP] Japan .................................. 2-275039

[51] Int. Cl.$^5$ .............................................. A61B 5/00
[52] U.S. Cl. .................................... 128/772; 604/280
[58] Field of Search ............... 128/657, 772; 604/95, 604/164, 280–283

[56] References Cited

U.S. PATENT DOCUMENTS 4,876,126 10/1989 Takamura ........................... 604/266
4,925,445 5/1990 Sakamoto et al. ................. 128/772

FOREIGN PATENT DOCUMENTS 113186 11/1983 European Pat. Off. .
141006 1/1984 European Pat. Off. .
379578 8/1988 European Pat. Off. .
340304 12/1989 European Pat. Off. .
1435797 10/1973 United Kingdom .

Primary Examiner—Max Hindenburg
Attorney, Agent, or Firm—Heller, Ehrman, White & McAuliffe

[57] ABSTRACT

A guide wire for a catheter is disclosed that includes a core wire and a sheath for covering at least the distal end of the core wire. The core wire is formed from a nickel-titanium alloy having a nickel-titanium ratio in the range of 3:2 to 1:1. The core wire is worked in a manner such that in a tensile test wherein the core wire is elongated by at least 5%, the core wire has a recovery percentage of at least 90%. Additionally, elongations in the range of zero and 5% do not cause any stress-induced martensitic transformations and/or austinite reverse transformations. Thus, the load-elongation characteristics of the nickel-titanium alloy are such that the load increasing rate is either proportional or gradually decreasing throughout the elongation range of 0 to 5%.

16 Claims, 6 Drawing Sheets

GUIDE WIRE FOR A CATHETER

This application claims the priority of Japanese Patent Application No. 2-275039 filed on Oct. 12, 1990 which is incorporated herein by reference.

BACKGROUND OF THE INVENTION

1. Field of the Invention

The present invention relates to a guide wire for guiding the insertion of a catheter into a blood vessel.

2. Description of the Related Art

A guide wire for a catheter is required to have several characteristics, including good flexibility as well as resilience against and recovery from deformation. Also, the guide wire has to be smoothly inserted into and along blood vessels within the human body, which branch and meander in the body, without damaging the blood vessel.

Conventionally, wires made of plastic, carbon steel, stainless steel or the like are used as the guide wires for catheters. More recently, guide wires having their core wire made of a superelastic metal, such as a nickel-titanium alloy have been proposed. See, for example, Japanese Laid open Patent Publication Nos. 2-24548, 2-24549 and 2-24550.

Superelasticity refers to a characteristic that, even if a material is strained beyond its yield point such that it appears to have undergone plastic deformation, when the external stress is relieved, the material returns to the original shape. As shown by the curve E3 FIG. 10, the load-elongation diagram for a superelastic alloy includes a horizontal portion P at which the resistance load of the alloy does not increase even as the alloy elongates. The load-elongation also has a proportional portion Q where the elongation and the load change proportionally. The superelastic alloy is therefore more flexible and more elongatable than other metals, such as stainless steel.

In the environment of a core wire of a catheter guide wire, if a sufficient load is applied to the core wire to bring the alloy into the horizontal portion P, the core wire merely elongates. This means that the guide wire becomes too flexible. Thus, it is difficult for the user to sense the movements and response of the guide wire during use and buckling occurs. This impedes the delicate control necessary to insert the guide wire into the blood vessel.

To overcome this shortcoming, some countermeasure may be taken to increase the diameter of the guide wire to give it a certain rigidity. Increasing of the diameter of the guide wire however restricts (or adversely influences) the operability of the guide wire. It also raises the cost of the guide wire, which is undesirable.

Further, increasing the diameter of the guide wire results in a steeper change of the previously described loadelongation curve. Thus, the characteristics of such a guide wire are not very different from the characteristics of the conventional stainless-steel wire. The use of such guide wires tend to be painful for the patients. For example they tend to be painful during removal because the shape of the guide wire tends to change some and the bent portions of the guide wire are difficult to pull back through the tortuous path of the blood vessels.

SUMMARY OF THE INVENTION

Accordingly, it is an object of the present invention to provide a guide wire for a catheter, which has flexibility and proper elasticity, and permits the catheter to be inserted into a desirable site in a blood vessel and to be settled there without damaging the blood vessel.

To achieve the foregoing and other objects and in accordance with the purpose of the present invention, an improved guide wire for a catheter is provided. The guide wire includes a core wire and a sheath for covering at least the tip portion or distal end of the core wire.

The core wire is formed from a nickel-titanium alloy having a nickel-titanium ratio in the range of 3:2 to 1:1. The core wire is worked in manner such that in a tensile test wherein the core wire is elongated by at least 5%, the core wire has a recovery percentage of at least 90%. Additionally, elongations in range of zero and 5% do not cause any stress-induced martensitic transformations and/or martensitic reverse transformations. Thus, the load-elongation characteristics of the nickel-titanium alloy are such that the load increasing rate is either proportional or gradually decreasing throughout the elongation range of 0 to 5%.

In one preferred embodiment, the alloy consists essentially of nickel and titanium and has a nickel content of 55.0 to 57.0%. In alternative preferred embodiments, up to five percent by weight of certain metals can also be added to the alloy.

In a method aspect of the invention, a nickel-titanium alloy wire is originally formed by either a diffusion method or a melting method. This alloy wire is then cold drawn to reduce its cross-sectional area in the range of 35 to 50%. The cold drawn wire is then heat treated at a temperature in the range of 350° to 400° C. for a time period in the range of 10 to 30 seconds.

In a preferred diffusion method of producing the alloy wire, a plurality of nickel plated titanium wires are bundled together to form a composite body. The composite body is then subject to cold drawing, heat diffusing treatment and a surface treatment. This resultant wire is then subject to the specific cold drawing and heat treating steps set forth above.

BRIEF DESCRIPTION OF THE DRAWINGS

The features of the present invention that are believed to be novel are set forth with particularity in the appended claims. The invention, together with the objects and advantages thereof, may best be understood by reference to the following description of the presently preferred embodiments together with the accompanying drawings in which:

DETAILED DESCRIPTION OF THE PREFERRED EMBODIMENT

Figure 1:
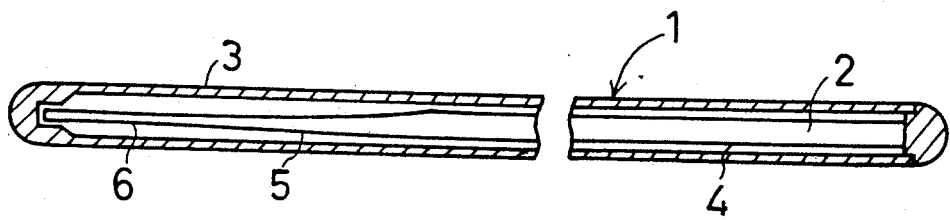
FIGS. 1 to 4 are longitudinal cross sectional views of various catheter guide wire designs that may include core wires formed in accordance with the present invention.

A preferred embodiment of the present invention will now be described referring to the accompanying drawings. As shown in FIGS. 1 through 4, a guide wire 1 comprises a core wire 2 made of a nickel-titanium alloy (hereinafter referred to as "Ni-Ti alloy") and a sheath 3 for covering the core wire 2.

The core wire 2 is an elongated member and includes a body 4 having a reference diameter. The distal end of the core wire has a reduced diameter tip portion 6. A tapered portion 5 links the body 4 and the distal tip portion 6. The diameter of the tapered portion 5 gradually decreases toward the distal end 6. The reference diameter of the body 4 is in a range of 0.2 to 1.0 mm, preferably 0.3 to 0.5 mm. The diameter of the distal end 6 is in a range of 0.05 to 0.2 mm. By way of example, a suitable length for the core wire is about 1500 mm.

Figure 2:
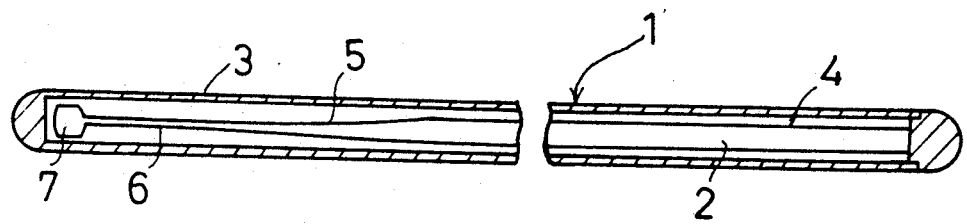

The core wire 2 may be designed to have the distal end 6 cut off such that it includes only the body 4 and the tapered portion 5. The tip of the distal end 6 may be provided with an enlarged bulb 7 having approximately the same diameter as that of the body 4, as shown in FIG. 2. The enlarged bulb 7 prevents the tip of the core wire 2 from piercing the distal end of the sheath 3.

Figure 8:
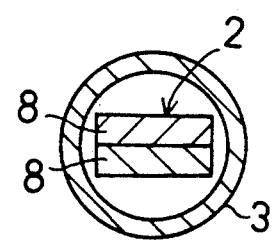
Figure 9:
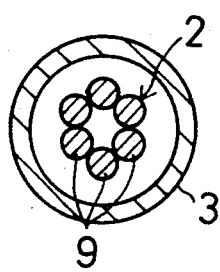

As shown in FIGS. 5 through 9, the core wire 2 may have a variety of cross sectional shapes. For example, the cross section may be circular (FIG. 5), elliptical, hexagonal (FIG. 6), flat rectangular (FIG. 7), or the like. The core wire 2 may also be formed from a pair of laminated core wire pieces 8 each having a rectangular cross section as shown in FIG. 8, or it may take the form of a multiplicity of wires 9 twisted together as shown in FIG. 9.

The sheath 3 is made of a macromolecular compound that is compatible with use in a human body. Suitable compounds include polyurethane, polyethylene, nylon, silicone resin, Teflon (or polytetrofluoroethylene), cellulose, starch, gelatin, and the like.

The sheath 3 may be shaped into a tube with one end sealed, as shown in FIGS. 1 and 2. Alternately, the sheath 3 may be directly coated on the outer surface of the core wire 2, as shown in FIGS. 3 and 4.

Figure 3:
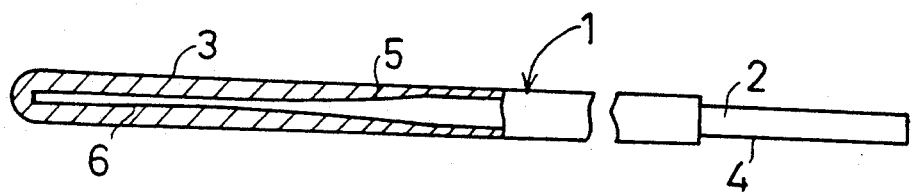
Figure 4:
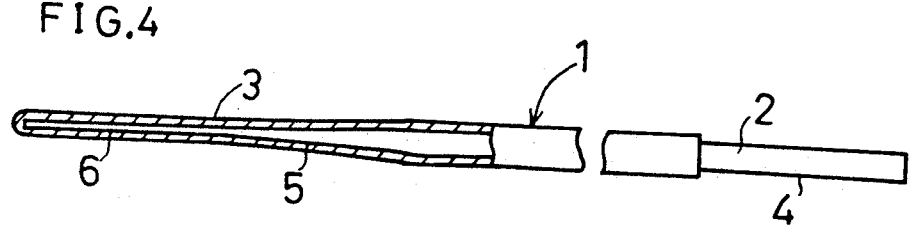
Figure 5:
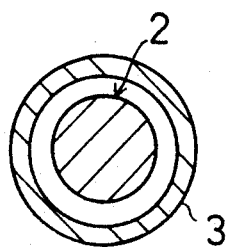
FIGS. 5 to 9 are transverse cross sectional views of various catheter guide wire designs that may include core wires formed in accordance with the present invention.
Figure 6:
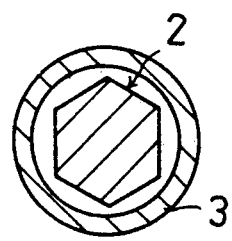
Figure 7:
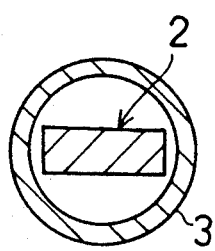

The sheath 3 may cover the entire core wire 2, as shown in FIGS. 1 and 2, or may be formed only over a portion of the core wire 2 with a predetermined length, which is to be inserted into a human body, as shown as FIGS. 3 and 4. It is preferable that the tip of the sheath 3 be shaped hemispherical.

To prevent tension from acting between the core wire 2 and the sheath 3 with the bending of the sheath 3, the core wire 2 is preferably provided slidable relative to the sheath 3. When the sheath 3 is coated on the outer surface of the core wire 2, therefore, it is preferable to precoat a lubricant on that surface of the core wire 2. The lubricant may be powder, liquid or a viscous material.

The Ni-Ti alloy for the core wire 2 has a nickel (Ni) to titanium (Ti) ratio in the range of 6:4 to 1:1. In a preferred embodiment the content of the alloy is just nickel and titanium with nickel constituting in the range of 50 to 60% by weight (preferably 54 to 57% by weight). Titanium (Ti) constitutes the remainder of the alloy. That is in the range of 40 to 50% by weight (preferably 43 to 46% by weight). Alternatively, an alloy having a third element, such as copper (Cu), aluminum (Al), iron (Fe), zinc (Zn) or cobalt (Co) may be used. If such an alloy is used, the content of the third element should be at most 5%. The Ni-Ti ratio would remain the same.

If the Ni-Ti alloy contains less than 50% by weight of nickel, the core wire 2 becomes too soft. If the nickel content is 60% by weight or above, the core wire 2 is not only too hard to work, but also becomes easy to break.

The Ni-Ti alloy is cold drawn with a large proportional drawing amount. That is, wire alloy is drawn sufficiently to reduce the cross-sectional area of the wire by a large amount during cold working. It is then shaped by heat treatment at a relatively low temperature. These drawing and heat treatment steps are instrumental in determining the load-elongation characteristic of the alloy.

By way of example, the cold drawing may reduce the cross-sectional area of the wire by in the range of 30 to 55% (preferably 35 to 50%) of its original area. This is referred to as a 30%-55% (35% to 50%) reducing percentage. The wire is then subjected to a heat treatment while maintaining the desired shape (e.g., a linear shape), thus yielding the core wire 2. It is preferable that the heat treatment be conducted at 350° to 450° C. (preferably 350° to 400° C.) for in the range of one second to five minutes (preferably in the range of 10 to 30 seconds).

The Ni-Ti alloy for the core wire 2, may be produced by either a melting method (hereinafter called "melted material") or by a diffusing method (hereinafter called "diffused material").

As disclosed in Japanese Unexamined Patent Publication No. 62-120467, a plurality of titanium-nickel wires each having nickel plated on a titanium wire are bundled together to be a composite body in the diffusing method. The composite body is subjected to cold drawing, a heat diffusing treatment, a surface treatment and so forth, and is then subjected to a post treatment to be provided with the mentioned characteristic, thus yielding a diffused material.

In the melting method, like an ordinary alloy, titanium and nickel are melted by heating, and the resultant melt is transferred into a mold to yield an ingot. This ingot is hot-rolled, and is repeatedly subjected to cold drawing and heat treatment until the ingot becomes a wire with the intended size. The resultant wire is then subjected to a post treatment (e.g., cold working or a heat treatment) to have the desired characteristic, yielding a melted material.

Since the titanium used in the melting method, oxidizes rather easily, it is somewhat difficult to control the composition of titanium and nickel at the melting time. It is also difficult to yield products with a uniform composition distribution, and crystal particles tend to increase metallographically. In general, therefore, the melting method cannot easily provide a wire having a diameter of 0.06 mm or less.

In contrast, when the diffusing method is used, titanium and nickel are mutually diffused to form an alloy. Thus, oxidization of the metal components is suppressed, which permits the alloy to have the desired composition. In addition, the diffusing method will provide finer crystal particles than the melting method, making it difficult for nonmetal impurities to be mixed into the alloy. Thus, diffused materials are superior in stability and uniform quality characteristics when compared to melted materials.

Further, the stress-strain characteristics (load-elongation characteristics) of diffused materials are excellent and can thus easily yield wires of 0.02 mm in diameter. When the diffusing method is used, only very minute amounts of oxide in a solid solution form is produced in the alloy. The small amount of oxide that does exist is scattered along the wire. Diffused materials therefore have high durability against stresses in their lengthwise direction.

As the raw material for the core wire 2 of the guide wire 1, a diffused material with a nickel content of 55.0 to 57.0% (preferably 55.5 to 56.5%) is suitable. Increasing of the nickel content can harden the diffused material more.

A core wire 2 of the diffused material can be acquired by subjecting the diffused Ni-Ti alloy to cold drawing with a cross-section reducing percentage in the range of 35 to 50%, then subjecting the alloy to a heat treatment at 350° to 400° C. for one second to five minutes (preferably 10 to 30 seconds). If a melted material having the same composition as this diffused material is used and is subjected to a heat treatment at a lower temperature than the level employed for the diffused material, the same load-elongation characteristic can be imparted to the melted material.

The guide wire 1 embodying the present invention is formed from the core wire 2 made of the above-described workhardened type Ni-Ti alloy. When a load is applied to this core wire 2 and the wire's load-elongation characteristics are measured in a tensile test, smooth changes are observed in both elongation and load characteristics. This is seen in Examples 1 and 2 to be described later. When the load is removed, the core wire 2 can recover the shape by a recovery percentage of over 90%.

The use of such a material enhances the operability of the guide wire, permits the user to better feel the response of the wire during insertion, and prevents possible occurrence of buckling.

A description will now be given of Examples 1 and 2 and a Comparative example which includes core wires 2 which are respectively made of the above-described diffused material, melted material and conventional superelastic material. The core wires 2 in each of these samples have the shape shown in FIGS. 1 and 5, a reference diameter of 0.4 mm, and are 1500 mm long.

The individual core wires 2 are subjected to a tensile test and a three point bending test to measure their strengths. The transformation points were measured using a differential scanning calorimeter (DSC).

Figure 10:
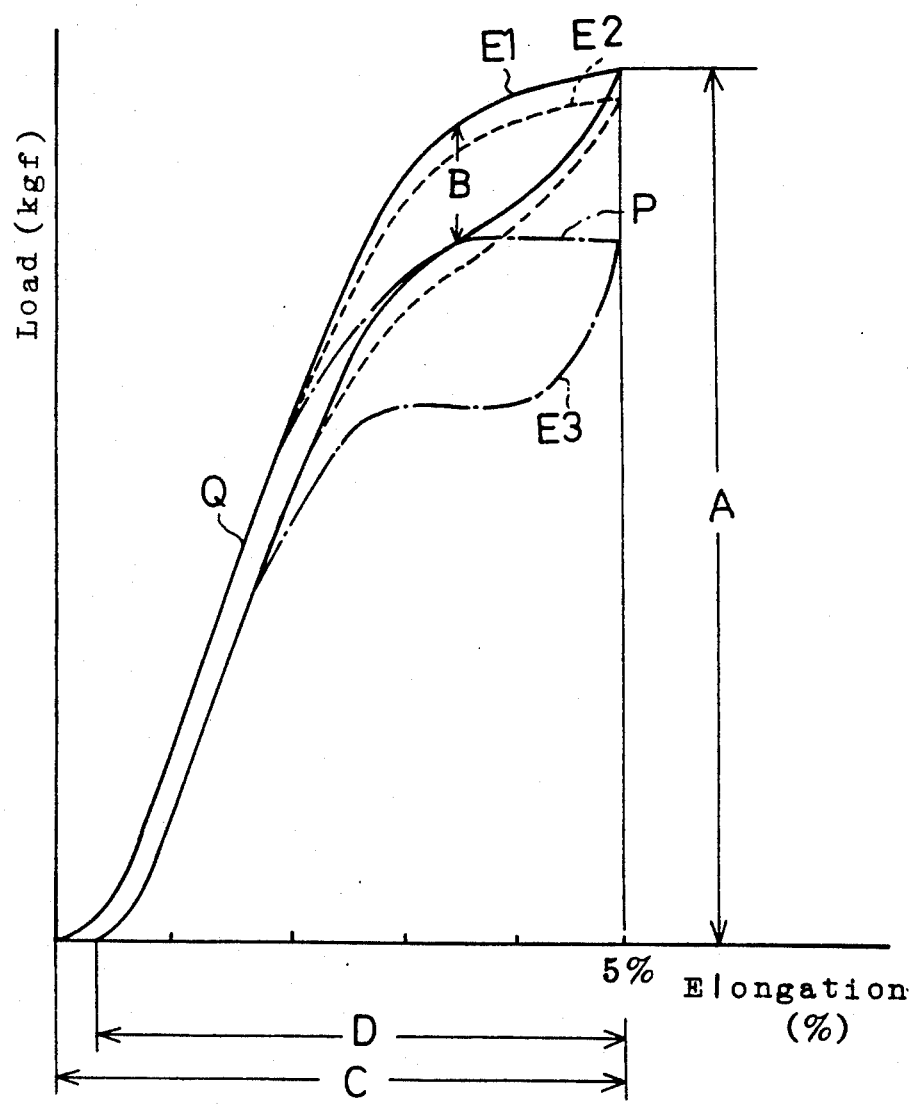
FIG. 10 is a graph comparing the load-elongation characteristics observed in a tensile test of two core wires made in accordance with the present invention to a core wire made of a superelastic material.
Figure 13:
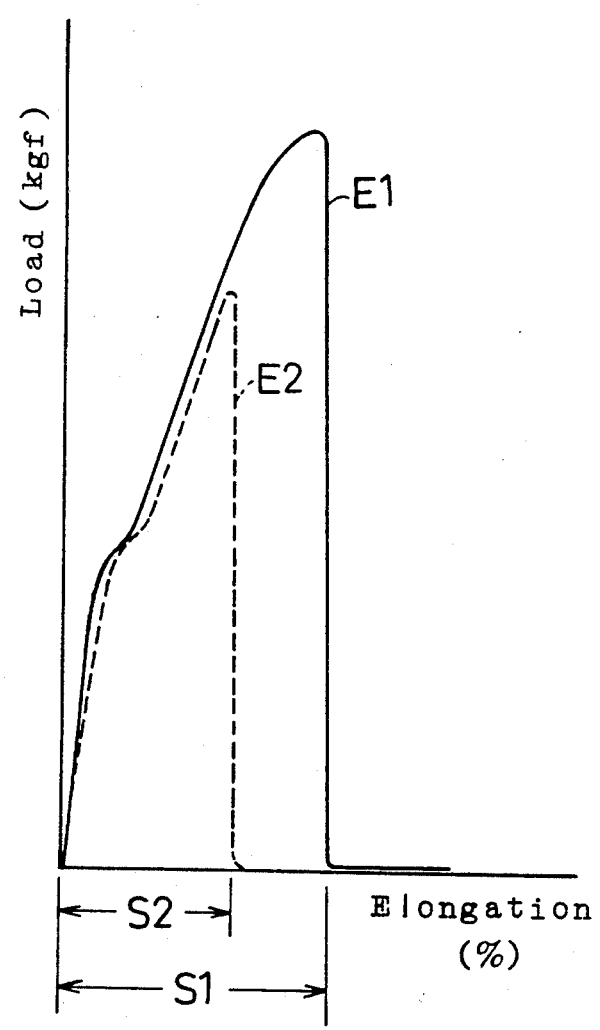
FIG. 13 is a graph showing the elongation and load characteristics of the two sample core wires of the present invention at failure.

In the tensile test, a load is first gradually applied to the samples to cause 5% strain (elongation). Thereafter, the load is gradually relieved. The relation between the load and the elongation when this sequence of load-applying and load-removing operations was conducted was measured. FIG. 10 illustrates the results of the measurement of the load-elongation characteristic. FIG. 13 shows the results of the measurement of the elongation at failure.

Figure 11:
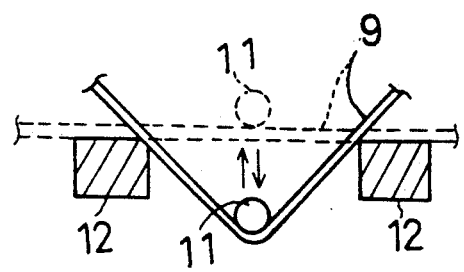
FIG. 11 is a schematic diagram illustrating a testing device for a three point bending test.
Figure 12:
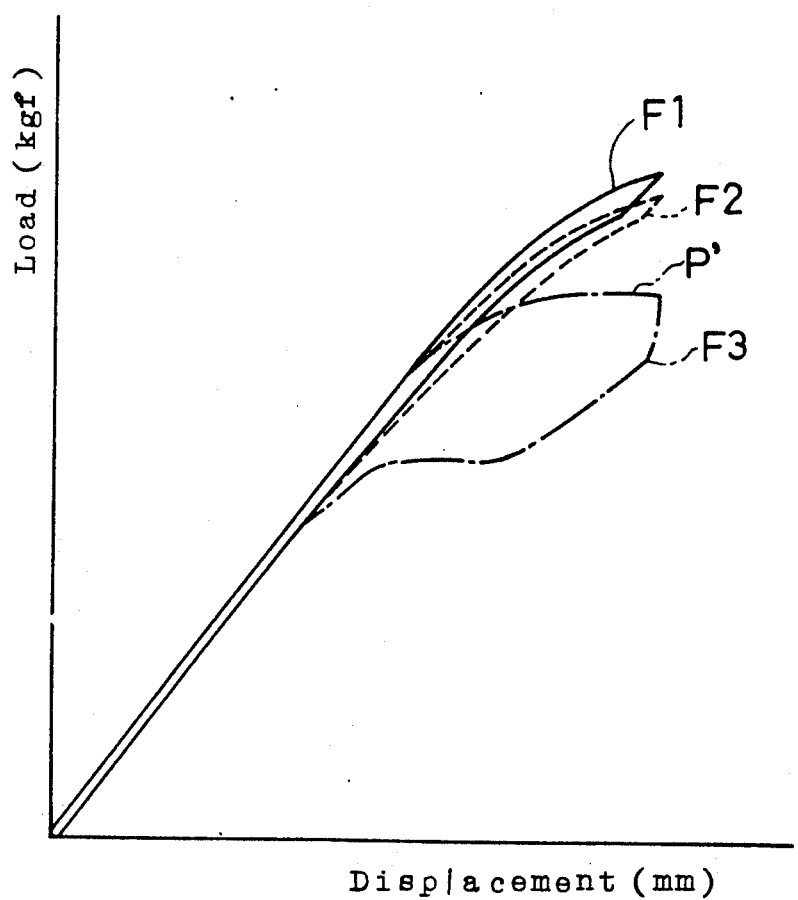
FIG. 12 is a graph showing the results of the three point bending test on the sample and comparative sample core wires shown in FIG. 10.

In the three point bending test, each core wire 2 is bridged over supports 12 that are 14 mm apart in an atmosphere at a temperature of 37° C., as shown in FIG. 11. A 5 mm diameter bar 11 is placed at the midpoint between the supports 12 and is pulled downward by a displacement of 2 mm at the rate of 2.0 mm/min to apply a load on the core 2. Then, the bar 11 is returned to the original position to remove the load on the core 2. The load the bar 11 receives when moving up and down is measured. FIG. 12 presents the relationship between the up-and-down displacement of the bar 11 and the measured load.

Figure 14:
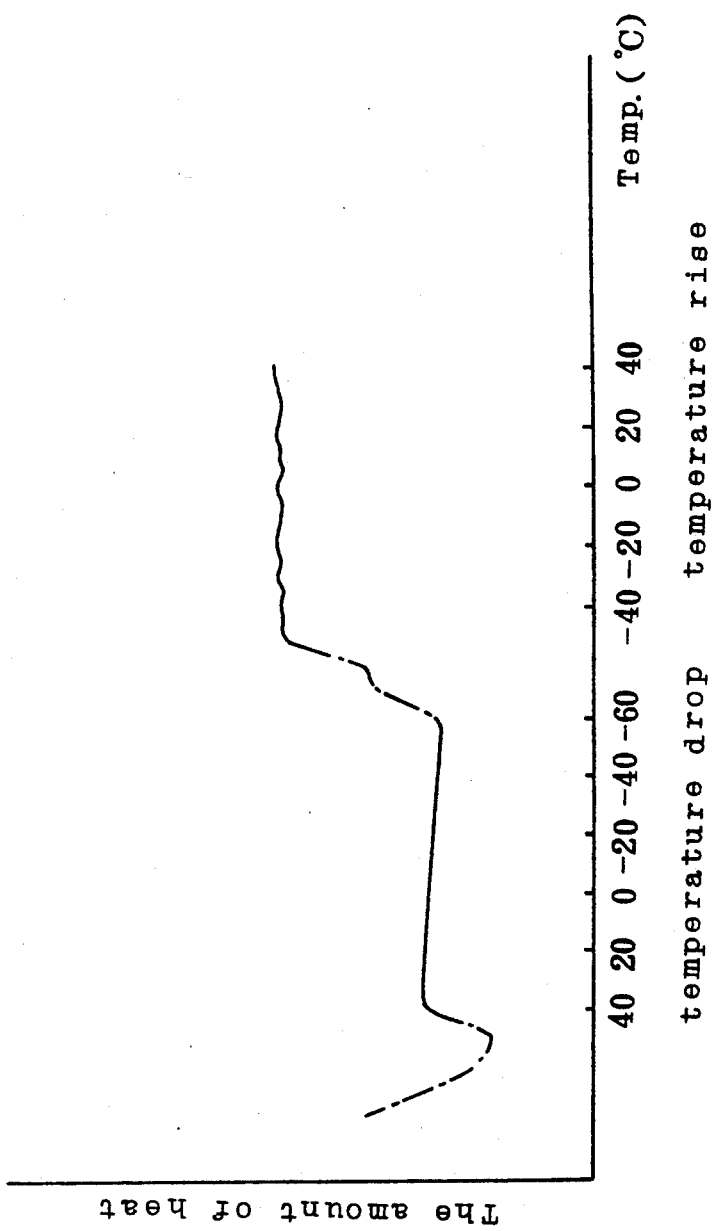
FIG. 14 is a graph showing the results of measurement done using a differential scanning calorimeter (DSC).

The DSC measured a change in the amount of heat caused by endothermic and exothermic reactions in the material. The temperature range examined covered the range of −60° to 50° C. FIG. 14 exemplifies the results of that measurement. As can be seen in that graph, there were no significant endothermic or exothermic reactions observed which shows that there are not any crystalline changes in the observed temperature range.

EXAMPLE 1

An alloy wire (Ni: 55.8% by weight, Ti: remainder) acquired by the diffusing method was subjected to cold drawing such that its cross-sectional area is reduced by 42% of its original area. Then, this wire was subjected to an aging treatment at 400° C. for 20 seconds while keeping the desired shape, thus yielding a linear core wire 2.

The results of the tensile test are represented by a curve E1 in FIG. 10, which shows a smooth increase in load with an increase in elongation. The curve E1 does not have a horizontal portion where the load is constant even as the elongation increases. In the region where the elongation (strain) is about 3% or lower, there is a proportional portion Q which shows the elongation almost proportional to the load. In the region where the elongation exceeds 3%, the curve portion following the proportional portion Q shows a gradual decrease in the load-increasing rate.

At 5% elongation, the maximum load (A) is 15 kg and the recovery percentage is 98% or above. The recovery percentage is expressed by the ratio D/C where C is the total elongation when the load is applied and D is the amount recovered when the load is relieved. The elongation at failure S1 is 32%. This core wire 2 showed an excellent performance as an elastic material.

The results of the three point bending test are shown by a curve F1 in FIG. 12. In this test, displacement likewise smoothly increases with an increase in load and smoothly decreases with a reduction in load.

FIG. 14 illustrates the results of the measurement by the DSC. As is apparent from the diagram, there are no peaks observed which indicate endothermic or exothermic reactions in either the temperature-raising process and the cooling process when undertaken in the temperature range of −60° to 50° C. Therefore, it is understood that the core wire 2 does not have a substantial transformation point in this temperature range.

EXAMPLE 2

An alloy wire (Ni: 55.8% by weight, Ti: remainder) acquired by the melting method was subjected to cold drawing such that its cross-sectional area is reduced to 50% of the original area. Then, this wire was subjected to an aging treatment at 370° C. for 30 seconds, thus yielding a linear core wire 2.

The results of the tensile test are represented by a curve E2 in FIG. 10, which shows a smooth increase in load with an increase in elongation, as in Example 1. The curve E2 also does not have a horizontal portion where the load is constant even the elongation increases.

At 5% elongation, the maximum load is 12 kg and the recovery percentage is 94%. The elongation at failure S2 is 17%. This core wire 2, like the one in Example 1, showed an excellent performance as an elastic material.

The results of the three point bending test are shown by a curve F2 in FIG. 12. As in Example 1, displacement likewise smoothly increases with an increase in load and smoothly decreases with a reduction in load. The recovery percentage of the core wire 2 in this test is the same as that acquired in the tensile test, indicating that this core wire 2 has a characteristic similar to that of an ordinary spring material.

As in Example 1, the results of the measurement by the DSC show no substantial transformation point in the temperature range of −60° to 50° C.

COMPARATIVE EXAMPLE

A nickel-titanium alloy wire (0.4 mm in diameter) having an Af point (Austinite finish point) of 6° C. in the measurement by the DSC was used as the core wire 2. The Af point is the end temperature of the reverse transformation from the martensite phase to the parent phase (austinite phase). This wire is superelastic and has a nickel content of 56.2% by weight.

The results of the tensile test are shown by the curve E3 in FIG. 10. The curve E3 has the horizontal portion P where the load is constant even as the elongation increases. The existence of the horizontal portion P is the characteristic of an alloy having superelasticity. In the range of the horizontal portion P, a phase change based on the deformation stress occurs, causing a stress-induced martensitic transformation. The results of the three point bending test are shown by a curve F3 in FIG. 12.

The core wires 2 in Examples 1 and 2 can recover the shape by a recovery percentage of 90% or greater when at least over 5% (more preferably at least 7%) of elongation is given in the sequence of load-applying and load-removing operations. The core wires 2 in Examples 1 and 2 have a characteristic such that the load-increasing rate gradually decreases after the load increases in proportion to an increase in elongation within the elongation range of 0 to 5% in the load-elongation characteristic. In this elongation range, therefore, the value of maximum load (A) of Example 1 or that of Example 2 can be set greater than the value of maximum load of the Comparative example.

The bending characteristics relate to the tensile characteristic, so that the core wires 2 of Examples 1 and 2 have a greater maximum load value at the time of bending than the core wire 2 of the Comparative example. Therefore, a core wire made from the material of examples 1 or 2, can effectively prevent buckling even when the wire 2 is thinner. Making the core wire 2 thinner results in cost reductions and enhances the operability of the guide wire when in use.

The ratio of the maximum load loss (B) to the maximum load (A), B/A, should be at most 0.3 (i.e. a 30% load loss) and preferably is 0.2 or below (i.e. at most a 20% load loss). With such load loss ratios, deformation of the core wire at the time of relieving the load can be effectively suppressed.

The maximum load value is defined as the maximum value of the load in a hysteresis curve drawn in accordance with the application and removal of the load, and indicates the value A when specified by the curve E1 in FIG. 10. The value of maximum load loss is defined as the maximum value of the difference between the line on the load-applying side (upper line) in the hysteresis curve and the line on the load-removing side (lower line), and indicates the value B in the curve E1 in FIG. 10.

The core wires 2 of Examples 1 and 2 do not have any substantial transformation point at which the stress-induced martensitic transformation reverse and/or martensitic reverse transformation occurs. Thus, even if these core wires are repeatedly bent when the guide wire 1 is inserted in a blood vessel, stress-induced martensitic transformations will not take place.

According to the present invention, as described above, it is unnecessary to consider the transformation temperature when producing the core wire 2. This facilitates control of the composition ratio, the working method, and the like. It also improves the product yield. Further, core wires according to the present invention have high elasticity at any temperature. This is because they have a relatively low occurrence of plastic deformation originating from excessive strain at temperatures equal to or lower than the transformation temperature. Such deformation is prominent in the prior art products. Because of the high elasticity, the core wire 2 does not lose its original shape and has an excellent recovery against buckling.

This can also be seen from the individual curves in FIG. 12, the core wires of Examples 1 and 2 both showing a high recovery percentage. Like the curve E3 in FIG. 10, the curve F3 has a horizontal portion P', which is the characteristic of a superelastic alloy. Because of the horizontal portion, a similarly sized conventional core wire has a smaller maximum load value. Accordingly, conventional wires have lower bending recovery properties which limit the wire's capabilities during insertion.

Even in the case where the guide wire embodying the present invention is bent during insertion, it can return to the original shape by a large recovery percentage because the guide wire has a large maximum load value with a relatively lower maximum load loss. These characteristics can correct the bending of a blood vessel to some extent when removing the guide wire, allowing for relatively soft and painless removal of the guide wire.

A description will now be given of the results of a clinical test to see the effects of the core wires of the previously-described Examples 1 and 2 according to the present invention as used in a guide wire in comparison with the core wire of the previously-described Comparative example.

The guide wires used in this clinical test are coated with a polyurethane resin and are shaped as shown in FIG. 4.

TABLE 1

|  | Example 1 | Example 2 | Comparative Example |
|---|---|---|---|
| Operability | 10 | 9.5 | 9 |
| Easy bending of distal end | 0 | 0 | Δ |
| Number of repeated bending | 3.3 | 0.67 | — |

In Table 1 above, the "operability" means how easy to insert the guide wire into a blood vessel. This reflects the feeling of persons undergoing the test at the time of wire insertion, as evaluated in the scale of 1 to 10 with the feeling for Example 1 taken as "10." The larger the value, the better the operability is.

In using a guide wire, its distal end may be deformed to have plastic deformation in one direction prior to insertion in some cases. The "easy bending of distal end" is the characteristic for evaluation of how easily that work is done. This was evaluated by bending the core wire at an arbitrary angle with fingers and checking if the bending had caused any deformation.

The "number of repeated bending" is the evaluation on the characteristic concerning the life of the guide wire. In this test the core wire was bent 170° with a bending radius of 1.5 mm and then released, and this sequence was repeated. The number of the repetition until the guide wire is broken is indicated by the average value for three core wires of each example.

In the test, every core wire of the Comparative example was broken in the first bending, and no measurement was therefore taken in this case.

The results of the clinical test as given in Table 1 show that the core wire of Example 1, made of diffused material, is superior in all the characteristics and is most preferable. Wit the use of the guide wire of the Comparative example, problems occurred several times, such as the wire piercing through the blood vessel and breaking the core wire. Due to the excellent characteristics of the core wire of the guide wire according to the present invention, however, the torque transmitting property and the response sensitivity (feeling) are enhanced, so that such problems would not have occurred at all. This is a very noteworthy event for guide wires.

Although only one embodiment of the present invention has been described herein, it should be apparent to those skilled in the art that the present invention may be embodied in many other specific forms without departing from the spirit or scope of the invention. Therefore, the present examples and embodiments are to be considered as illustrative and not restrictive an the invention is not to be limited to the details given herein, but may be modified within the scope of the appended claims.

What is claimed is:

1. A guide wire for a catheter comprising:
   a core wire formed from a nickel-titanium alloy having a nickel-titanium ratio by weight in the range of 3:2 to 1:1, the core wire being fashioned such that in a tensile test wherein the core wire is elongated by at least 5%, the core wire has a recovery percentage of at least 90%, and such that elongations of 5% do not cause any martensitic transformations or martensitic reverse transformations; and
   a sheath for covering at least a distal end of the core wire.

2. The guide wire according to claim 1, wherein the loadelongations characteristics of the nickel-titanium alloy are such that the load increasing rate is either proportional or gradually decreasing throughout the elongation range of 0.8 to 5%.

3. The guide wire according to claim 1, wherein the core wire has such a characteristic that a ratio (B/A) of a value of maximum load loss (B) to a value of maximum load (A) is at most 0.3 in the elongation range of 0% to 5%.

4. The guide wire according to claim 1, wherein the nickel-titanium alloy consists essentially of nickel and titanium and has a nickel content i the range of 50% to 60% by weight.

5. The guide wire according to claim 4, wherein the nickel-titanium alloy is produced by a diffusing method and has a nickel content of 55.0% to 57.0%.

6. The guide wire according to claim 1, wherein the nickel-titanium alloy includes a third element selected from a group consisting of copper, aluminum, iron, zinc and cobalt, the third element constituting at most 5% of the alloy by weight.

7. The guide wire according to claim 1, wherein the core wire has a body portion of 0.2 mm to 1.0 mm in diameter.

8. The guide wire according to claim 1, wherein the core wire has a tapered portion whose cross-sectional area continuously decreases toward the distal end.

9. The guide wire according to claim 1, wherein the core wire has an enlarged bulb at the distal end.

10. The guide wire according to claim 1, wherein the sheath is made of a macromolecular compound selected from a group consisting of polyurethane, polyethylene, nylon, silicone resin, Teflon, cellulose, starch, and gelatin.

11. The guide wire according to claim 1, wherein the temperature in the range of −60° C. and 50° C. does not cause the core wire to make any martensitic transformations or martensitic reverse transformations.

12. A guide wire for a catheter comprising:
   a core wire made of nickel-titanium alloy consisting essentially of nickel and titanium and being produced by a diffusing method, the nickel content of the core wire being in the range of 55.0% to 57.0% by weight; the core wire being fashioned such that in a tensile test wherein the core wire is elongated by at least 5%, the core wire has a recovery percentage of at least 90%, and such that elongations of 5% do not cause any martensitic transformations or martensitic reverse transformations the load-elongations characteristics of the nickel-titanium alloy being such that the load increasing rate is either proportional or gradually decreasing throughout the elongation range of 9% to 5%; and
   a sheath for covering at least a distal end of the core wire, the sheath being made of a macromolecular compound selected from a group consisting of polyurethane, polyethylene, nylon, silicone resin, polytetrafluoroethylene, cellulose, starch, and gelatin.

13. The guide wire according to claim 12, wherein the core wire has a characteristic such that a ratio (B/A) of a value of maximum load loss (B) to a value of maximum load (A) is at most 0.3 in the elongation range of 0% to at least 5%.

14. The guide wire according to claim 12, wherein the core wire has a body portion having a diameter in the range of 0.2 mm to 1.0 mm, and a tapered portion having a cross-sectional area that continuously decreases toward the distal end.

15. The guide wire according to claim 12, wherein the temperature in the range of −60° C. and 50° C. does not cause the core wire to make any martensitic transformations or martensitic reverse transformations.

16. A guide wire for a catheter comprising:
   a core wire formed from a nickel-titanium alloy having a nickel-to-titanium ratio by weight in the range of 3:2 to 1:1,
   the core wire being produced by subjecting the nickel-titanium alloy to cold drawing to reduce its cross-section by 35% to 50% and heat-treating the cold drawn alloy at a temperature of 350° C. to 400° C. for 10 seconds to 30 seconds, whereby the core wire is fashioned such that in a tensile test in which the core wire is elongated by at least 5%, the core wire has a recovery percentage of at least 90%, and such that elongations of 5% do not cause any martensitic transformations or martensitic reverse transformations; and
   a sheath for covering at least a distal end of the core wire.

* * * * *